United States Patent
Aboohi et al.

(10) Patent No.: US 10,211,534 B2
(45) Date of Patent: *Feb. 19, 2019

(54) SILDENAFIL SOLUTIONS AND METHODS OF MAKING AND USING SAME

(71) Applicant: Vigorous Solutions Ltd., Kiryat Yearim (IL)

(72) Inventors: Morris Aboohi, Tel Aviv (IL); Moshe Rogosnitzky, Kiryat Yearim (IL)

(73) Assignee: Vigorous Solutions Ltd., Kiryat Yearim (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/951,197

(22) Filed: Apr. 12, 2018

(65) Prior Publication Data

US 2018/0233823 A1 Aug. 16, 2018

Related U.S. Application Data

(60) Division of application No. 15/256,897, filed on Sep. 6, 2016, which is a continuation-in-part of application No. PCT/IB2015/052014, filed on Mar. 19, 2015.

(60) Provisional application No. 61/955,299, filed on Mar. 19, 2014.

(51) Int. Cl.

| | | |
|---|---|---|
| *A61K 31/519* | (2006.01) | |
| *H01Q 5/55* | (2015.01) | |
| *A61K 9/00* | (2006.01) | |
| *A61K 47/08* | (2006.01) | |
| *A61K 9/68* | (2006.01) | |
| *A61K 47/10* | (2017.01) | |
| *A61K 9/08* | (2006.01) | |
| *H01Q 1/28* | (2006.01) | |
| *H01Q 1/36* | (2006.01) | |

(52) U.S. Cl.
CPC .............. *H01Q 5/55* (2015.01); *A61K 9/006* (2013.01); *A61K 9/0056* (2013.01); *A61K 9/0058* (2013.01); *A61K 9/08* (2013.01); *A61K 31/519* (2013.01); *A61K 47/08* (2013.01); *A61K 47/10* (2013.01); *H01Q 1/288* (2013.01); *H01Q 1/36* (2013.01)

(58) Field of Classification Search
CPC ...... A61K 31/519; A61K 47/08; A61K 47/10; A61K 9/0056; A61K 9/0058; A61K 9/006; A61K 9/08
See application file for complete search history.

(56) References Cited

U.S. PATENT DOCUMENTS

| | | |
|---|---|---|
| 6,531,114 B1 | 3/2003 | Gmunder |
| 6,548,490 B1 | 4/2003 | Doherty, Jr. |
| 6,552,024 B1 | 4/2003 | Chen |
| 6,592,850 B2 | 7/2003 | Gmunder |
| 6,923,988 B2 | 8/2005 | Patel |
| 7,166,299 B2 | 1/2007 | Yoo |
| 7,611,728 B2 | 11/2009 | Kidane |
| 7,618,976 B2 | 11/2009 | Braude |
| 7,879,828 B2 | 2/2011 | Wyeth |
| 8,517,982 B2 | 8/2013 | Perovitch |
| 8,642,270 B2 | 2/2014 | Leyland-Jones |
| 9,186,321 B2 | 11/2015 | Bergstrom |
| 9,968,609 B2 * | 5/2018 | Aboohi ................ A61K 9/0056 |
| 2002/0040139 A1 | 4/2002 | Billotte et al. |
| 2003/0216407 A1 | 11/2003 | Butt et al. |
| 2008/0317923 A1 | 12/2008 | Ley |
| 2009/0010958 A1 | 1/2009 | Pinney |
| 2013/0203767 A1 | 8/2013 | Butrous et al. |

FOREIGN PATENT DOCUMENTS

| | | |
|---|---|---|
| CA | 2858364 C | 7/2018 |
| EP | 18161634 | 12/2018 |
| IN | WO 01/35926 | 5/2001 |
| WO | WO2001035926 | 5/2001 |
| WO | WO2002005820 | 1/2002 |
| WO | WO2009125415 | 10/2009 |
| WO | WO2013093456 | 6/2013 |
| WO | WO2015140748 | 9/2015 |

OTHER PUBLICATIONS

Benavente Garcia et al. (2001) J. Agric. Food Chem. 49:189-191.
Bhatt et al. (2005) Chem. Commun., 2005,1073-1075.
Banerjee et al. (2006) Crystal Growth and Design 6(6):1468-1478.
Dogrell (2005) Expert Opin Pharmacother 6(1):75-84 [Abstract].
Farjami & Jouyban (2015) Solubility of Tadalafil in Pharmaceutical Solvent Mixtures at 298.2K, Chemical Engineering Communications, 202:11,1522-1527.
EMA SPAR Summary for Viagra (2016) [EMA/17073/2016].
Sawatdee et al., Why Sildenafil and sildenafil citrate monohydrate crystals are not stable, Saudi Pharmaceutical Journal, 2015, p. 504-515, vol. 23(5), Saudi Pharmaceutical Society/Elsevier.
Jung et al., Comparison of the solubility and pharmacokinetics of sildenafil salts, Archives of Pharmacal Research, 2011, p. 451-454, vol. 34(3), Pharmaceutical Society of Korea/Springer.
Wang et al., Mechanistic analysis of pH-dependent solubility and trans-membrane permeability of amphoteric compounds: application to sildenafil, International Journal of Pharmaceutics, 2008, p. 217-224, vol. 352, Elsevier.
Sawatdee et al., Enhanced dissolution of sildenafil dry foam tablets, Asian Journal of Pharmaceutical Sciences, 2016, p. 191-192, vol. 11(1), Asian Federation for Pharmaceutical Sciences/Elsevier.
"Inactive Ingredient Search for Approved Drug Products" http://www.accessdata.fda.gov/scripts/cder/iig/getiigWEB.cfm Oct. 24, 2013.
Appendix 6. Toxicological Data for Class 3 Solvents p. 3 acetone 1990.
Appendix 6. Toxicological Data for Class 3 Solvents pp. 23-25 ethanol 1996.

(Continued)

*Primary Examiner* — Audrea B Coniglio
*Assistant Examiner* — Audrea Buckley
(74) *Attorney, Agent, or Firm* — IPAttitude Ltd.; S. Yarus

(57) ABSTRACT

A pharmaceutical composition comprising a liquid carrier comprising water and at least 35% of ethanol and sildenafil citrate dissolved in said liquid carrier at a concentration of at least 7 mg/ml.

20 Claims, 4 Drawing Sheets

(56) References Cited

OTHER PUBLICATIONS

Appendix 6. Toxicological Data for Class 3 Solvents pp. 49-52 propanol 1992.
Badwan "Sildenafil Citrate" Analyt. Prof. Drug Subst. and Excip. vol. 27 pp. 339-376 2001 Academic Press.
Viagra® product insert; Pfizer Labs New York NY Jan. 2010.
EMEA 564519/2009 "CHMP Assessment Report for Vizarsin" 2009.

* cited by examiner

400

Identify patient taking customary dose of sildenafil citrate in solid form for erectile dysfunction (410)

↓ treat patient with sildenafil citrate in solution using a reduced dose which is less than 50% of customary dose (420)

SILDENAFIL SOLUTIONS AND METHODS OF MAKING AND USING SAME

RELATED APPLICATIONS

This application is a divisional of U.S. Ser. No. 15/256,897 having the same title and inventors and filed on Sep. 15, 2016 which is currently pending;

U.S. Ser. No. 15/256,897 was a continuation in part of PCT/IB2015/052014 filed Mar. 19, 2015 and later published as WO/2015/14078 and having the same title and inventors as the present application;

PCT/IB2015/052014 claimed the benefit under 35 U.S.C. § 119(e) of provisional application U.S. 61/955,299 filed Mar. 19, 2014 and having the same title and inventors as the present application;

Each of these three of related applications are fully incorporated herein by reference.

FIELD OF THE INVENTION

Various exemplary embodiments of the invention relate to pharmaceutical compositions containing sildenafil citrate as an active ingredient and to methods of producing and/or administering such compositions.

BACKGROUND OF THE INVENTION

Sildenafil as citrate is FDA and EMEA approved for treatment of erectile dysfunction and pulmonary arterial hypertension (PAH).

There are also reports that sildenafil citrate is used for off-label indications including, but not limited to, prevention of high-altitude pulmonary edema associated with altitude sickness, treating lung fibrosis, primary pulmonary hypertension, secondary pulmonary hypertension, hypoxia induced pulmonary hypertension, neonatal pulmonary hypertension, pediatric pulmonary hypertension, nonoperable chronic thromboembolic pulmonary hypertension, severe coronary artery disease, age-related macular degeneration, brachial artery flow-mediated dilatation (in type 2 diabetes), Raynaud's syndrome, anal fissures, postmenopausal female sexual dysfunction, female sexual arousal disorder, digital ulcers secondary to systemic sclerosis, migraine, premature ejaculation, sickle-cell disease with pulmonary hypertension, achalasia (esophageal motility dysfunction), severe digital ischemia, recurrent ischemic priapism, severe lymphatic formation, congestive heart failure, diastolic dysfunction, tunical fibrosis, multiple sclerosis, intrauterine growth restriction, chronic pelvic pain, Alzheimer's disease, stroke, preeclampsia, gastroparesis, glucose dyscontrol in diabetes, primary dysmenorrheal pain, for increasing exercise capacity during hypoxia, increasing uterine artery blood flow and endometrial thickness to promote in-vitro fertilization (IVF).

Sildenafil citrate has also been proposed as a treatment for prostate cancer, pancreatic cancer, ovarian cancer, stomach cancer, obesity, Crohn's disease, spastic esophageal disorder, reduction of alcohol induced gastric damage and other conditions.

Sildenafil citrate is commonly marketed as VIAGRA® (for treatment of erectile dysfunction) and REVATIO® (for treatment of pulmonary hypertension), both manufactured by Pfizer Pharmaceuticals. Generic versions of sildenafil citrate are also available. VIAGRA® is commonly supplied as 25, 50 or 100 mg tablets and is to be taken not more than once per day 0.5 to 4 hours prior to intercourse. REVATIO® is most often supplied as 20 mg tablets to be taken 3 times daily. Sildenafil citrate are often labeled with the amount of sildenafil so that the actual amount of sildenafil citrate is about 30% more than the dosage/tablet indicated on the label.

REVATIO® is also available in injectable form as a clear colorless, sterile, ready to use solution containing 10 mg of sildenafil citrate per 12.5 ml of solution. Each ml of solution contains 1.124 mg sildenafil citrate, 50.5 mg dextrose and water for injection.

The injectable form of REVATIO® is most often administered intravenously. This route of administration is practical in a hospital setting but impractical outside a hospital or clinic setting.

In the EU sildenafil citrate is also available as an oral suspension at a concentration of 10 mg/ml. REVATIO® POS (powder for oral suspension) is supplied by Pfizer to be made up into an oral suspension. Additional ingredients in the POS include colloidal silicon dioxide, sucralose, sorbitol, sodium benzoate, sodium citrate, flavor and xanthan gum. The active ingredient in suspension has a slower absorption rate than would be expected for a solution with a similar concentration. In addition, the presence of some of the additional ingredients makes this product difficult to tolerate for people with known sensitivities to these ingredients.

Whether provided as tablets or oral suspension, sildenafil citrate exhibits an absolute bioavailability of about 41% and is reported to result in maximum observed plasma concentrations within 30 to 120 minutes following oral dosing in a fasted state. The rate of absorption is reportedly reduced if taken with a high fat meal.

According to the US package insert for VIAGRA®, solubility of sildenafil citrate in water is 3.5 mg/ml. The EMEA CHMP Assessment Report For Vizarsin (International Nonproprietary Name: sildenafil) indicates that it is insoluble in ethanol, chloroform and acetone but soluble in methanol and dimethylsulfoxide (DMSO). The Jordanian Pharmaceutical Manufacturing Co. reports that sildenafil citrate is about 3.5 times less soluble in ethanol than in water (~1 mg/ml). The low water solubility of sildenafil citrate and/or its high presystemic elimination each independently contribute to its low oral bioavailability.

SUMMARY OF THE INVENTION

A broad aspect of the invention relates to use of sildenafil citrate as a pharmaceutically active ingredient.

One aspect of some embodiments of the invention relates to increasing bioavailability of sildenafil citrate. In some exemplary embodiments of the invention, bioavailability of sildenafil citrate is increased by providing the sildenafil citrate in solution at a concentration of 7, 10, 20, 25, 30, 35, 40, or 45 mg/ml or intermediate or greater concentrations As used in this specification and the accompanying claims the terms "in solution", "dissolved", "soluble" and variations thereof indicate transparency under light with no particles visible to the naked eye.

One aspect of some embodiments of the invention relates to dissolving the sildenafil citrate in water mixed with one or more alcohols. In some exemplary embodiments of the invention, the one or more alcohols includes ethanol. In some exemplary embodiments of the invention, a ketone, (e.g. acetone) is provided with the water and alcohol. In some exemplary embodiments of the invention, the solution is delivered to a patient as a spray. In some embodiments, the spray is delivered to the trachea and/or lungs using a nebulizer or a metered dose inhaler.

Another aspect of some embodiments of the invention relates to treatment methods for erectile dysfunction which rely on dosages of sildenafil citrate which are less than half of what the specific patient is used to taking. In some exemplary embodiments of the invention, dissolution of the sildenafil citrate and/or increased absorption due to the rapid uptake of the carrier contributes to the dosage reduction. According to various exemplary embodiments of the invention the administration route is oral or buccal.

It will be appreciated that the various aspects described above relate to solution of technical problems related to the low bioavailability of sildenafil citrate in solid or suspension formulations. Specifically, it is believed that the low solubility of sildenafil citrate tablets and/or suspension under physiologic conditions contributes to elimination of a significant amount of the ingested material without absorption.

Alternatively or additionally, it will be appreciated that the various aspects described above relate to solution of technical problems related to the relatively long time between drug administration and onset of desired therapeutic action. Specifically, experienced subjects reported half the time (or less) for the same therapeutic effect when using a solution as described above compared to a tablet form of sildenafil citrate.

Alternatively or additionally, it will be appreciated that the various aspects described above relate to solution of technical problems related to reducing the effective dose of sildenafil citrate. Specifically half the dose (or less) of sildenafil citrate in a solution as described above provides the same therapeutic effect compared to a tablet form or suspension form of sildenafil citrate.

Alternatively or additionally, it will be appreciated that the various aspects described above relate to solution of technical problems related to mitigation of unwanted side effects of sildenafil citrate.

In some exemplary embodiments of the invention there is provided a pharmaceutical composition including: (a) a liquid carrier including water and at least 20% of at least one alcohol; and (b) sildenafil citrate dissolved in the liquid carrier at a concentration of at least 7 mg/ml. In some embodiments, the liquid carrier includes at least 5% water. Alternatively or additionally, in some embodiments the liquid carrier includes at least 30% water. Alternatively or additionally, in some embodiments the concentration of sildenafil citrate dissolved in the liquid carrier is at least 12.5 mg/ml. Alternatively or additionally, in some embodiments the concentration of sildenafil citrate dissolved in the liquid is at least 20 mg/ml. Alternatively or additionally, in some embodiments the at least one alcohol includes ethanol. Alternatively or additionally, in some embodiments the liquid carrier includes a ketone. Alternatively or additionally, in some embodiments the ketone includes acetone. Alternatively or additionally, in some embodiments the liquid carrier includes more than 3% ketone. Alternatively or additionally, in some embodiments the concentration of the sildenafil citrate dissolved in the liquid is at least 25 mg/ml. Alternatively or additionally, in some embodiments, the pharmaceutical composition includes a flavoring agent. Alternatively or additionally, in some embodiments the pharmaceutical composition includes a bitterness blocking agent.

In some exemplary embodiments of the invention, there is provided an oral dosage form including: an outer coating; and a liquid core including a pharmaceutical composition as described hereinabove.

In some exemplary embodiments of the invention, there is provided buccal dosage form including: a carrier containing a pharmaceutical composition as described hereinabove; and a wrapper adapted to prevent evaporation of the liquid carrier during storage.

In some exemplary embodiments of the invention, there is provided treatment kit including: a container holding a plurality of doses of a pharmaceutical composition as described hereinabove; and a measuring device calibrated for measurement of a single dose from the container.

In some exemplary embodiments of the invention, there is provided treatment kit including: a plurality of single doses of a pharmaceutical composition as described hereinabove, each of the single doses contained in a separate container; and packaging material adapted to hold the separate containers.

In some exemplary embodiments of the invention there is provided a method including: (a) placing sildenafil citrate in a combination consisting essentially of one or more alcohols and water to produce a mixture; and (b) heating the mixture to produce a solution of the sildenafil citrate with a concentration of at least 7 mg/ml.

In some embodiments, the heating is to a temperature of at least 40° C., at least 45° C., at least 50° C., at least 55° C., at least 60° C., at least 65° C. or intermediate or lower temperatures. In some embodiments application of ultrasonic energy serves as a substitute for heating. Alternatively or additionally, in some embodiments the heating is to a temperature not exceeding 85 OC. Alternatively or additionally, in some embodiments the heating is conducted in an open container. Alternatively or additionally, in some embodiments the heating is conducted in a closed container. Alternatively or additionally, in some embodiments the solution of the sildenafil citrate has a concentration of at least 12.5 mg/ml. Alternatively or additionally, in some embodiments the one or more alcohols includes ethanol. Alternatively or additionally, in some embodiments the combination of one or more alcohols and water includes at least 20% alcohol. Alternatively or additionally, in some embodiments the combination of one or more alcohols and water includes at least 5% water. Alternatively or additionally, in some embodiments a volume of the solution after heating is substantially the same as a volume of the mixture prior to heating. Alternatively or additionally, in some embodiments a volume of the solution after heating is significantly less than a volume of the mixture prior to heating. Alternatively or additionally, in some embodiments the method includes cooling the solution and adding alcohol and/or water.

In some exemplary embodiments of the invention there is provided a method including: (a) providing a first volume of a ketone; (b) adding a second volume consisting essentially of one or more alcohols and water to produce a total volume of solution; and (c) dissolving sildenafil citrate at a concentration of at least 7 mg/ml with respect to the total volume.

In some embodiments, the method includes heating the solution at a temperature not less than 5° C. below the boiling point of the ketone. Alternatively or additionally, in some embodiments the heating is to a temperature at least 5° C. above a boiling point of the ketone. Alternatively or additionally, in some embodiments the heating is to a temperature at least 10° C. above a boiling point of the ketone. Alternatively or additionally, in some embodiments the method includes removing at least 25% of the ketone. Alternatively or additionally, in some embodiments the sildenafil citrate in the solution has a concentration of at least 25 mg/ml. Alternatively or additionally, in some embodiments the one or more alcohols includes ethanol. Alternatively or additionally, in some embodiments the combination of one or more alcohols and water includes at least 20% alcohol. Alternatively or additionally, in some embodiments the combination of one or more alcohols and water includes at least 5% water. Alternatively or additionally, in some embodiments a volume of the solution after heating is 50% or less of the volume of the solution prior to heating. Alternatively or additionally, in some embodiments the method includes cooling the solution and adding alcohol(s) and/or water to a total alcohol concentration of at least 34%.

In some exemplary embodiments of the invention there is provided a pharmaceutical composition including: (a) a liquid carrier including water, ethanol, and less than 20% acetone; and (b) sildenafil citrate dissolved in the liquid carrier at a concentration of at least 10 mg/ml.

In some exemplary embodiments of the invention there is provided pharmaceutical composition including: (a) a liquid carrier consisting essentially of water and at least 20% of at least one alcohol; and (b) sildenafil citrate dissolved in the liquid carrier at a concentration of at least 7 mg/ml. In some embodiments the liquid carrier includes at least 5% water. Alternatively or additionally, in some embodiments the liquid carrier includes at least 30% water. Alternatively or additionally, in some embodiments the concentration of sildenafil citrate dissolved in the liquid carrier is at least 12.5 mg/ml. Alternatively or additionally, in some embodiments the concentration of sildenafil citrate dissolved in the liquid is at least 20 mg/ml. Alternatively or additionally, in some embodiments the at least one alcohol includes ethanol. Alternatively or additionally, in some embodiments the liquid carrier includes a ketone.
Alternatively or additionally, in some embodiments the ketone includes acetone. Alternatively or additionally, in some embodiments the liquid carrier includes more than 3% ketone. Alternatively or additionally, in some embodiments the concentration of the sildenafil citrate dissolved in the liquid is at least 25 mg/ml. Alternatively or additionally, in some embodiments the pharmaceutical composition includes a flavoring agent. Alternatively or additionally, in some embodiments the pharmaceutical composition includes a bitterness blocking agent.

In some exemplary embodiments of the invention, there is provided an oral dosage form including: an outer coating; and a liquid core including a pharmaceutical composition as described hereinabove.

In some exemplary embodiments of the invention, there is provided buccal dosage form including: a carrier containing a pharmaceutical composition as described hereinabove; and a wrapper adapted to prevent evaporation of the liquid carrier during storage.

In some exemplary embodiments of the invention, there is provided treatment kit including: a container holding a plurality of doses of a pharmaceutical composition as described hereinabove; and a measuring device calibrated for measurement of a single dose from the container.

In some exemplary embodiments of the invention, there is provided treatment kit including: a plurality of single doses of a pharmaceutical composition as described hereinabove, each of the single doses contained in a separate container; and packaging material adapted to hold the separate containers.

In some exemplary embodiments of the invention there is provided a pharmaceutical composition including: (a) a liquid carrier consisting essentially of water, ethanol, and less than 20% acetone; and (b) sildenafil citrate dissolved in the liquid carrier at a concentration of at least 10 mg/ml.

Unless otherwise defined, all technical and scientific terms used herein have the same meaning as commonly understood by one of ordinary skill in the art to which this invention belongs. Although suitable methods and materials are described below, methods and materials similar or equivalent to those described herein can be used in the practice of the present invention. In case of conflict, the patent specification, including definitions, will control. All materials, methods, and examples are illustrative only and are not intended to be limiting.

As used herein, the terms "comprising" and "including" or grammatical variants thereof are to be taken as specifying inclusion of the stated features, integers, actions or components without precluding the addition of one or more additional features, integers, actions, components or groups thereof. This term is broader than, and includes the terms "consisting of" and "consisting essentially of" as defined by the Manual of Patent Examination Procedure of the United States Patent and Trademark Office. Thus, any recitation that an embodiment "includes" or "comprises" a feature is a specific statement that sub embodiments "consist essentially of" and/or "consist of" the recited feature.

The phrase "adapted to" as used in this specification and the accompanying claims imposes additional structural limitations on a previously recited component.

The term "method" refers to manners, means, techniques and procedures for accomplishing a given task including, but not limited to, those manners, means, techniques and procedures either known to, or readily developed from known manners, means, techniques and procedures by practitioners of chemistry and/or pharmacology.

Percentages (%) of solvents (e.g. water and/or alcohols and/or ketones) indicate preparing a total volume (T) by measuring a volume (X) of a first liquid and adding a second liquid until the total volume teaches T. For example, to prepare one liter of a 70% ethanol solution 736.8 ml of 95% ethanol is measured and water is added to a total volume of 1 liter. Such a solution is also referred to here as 70:30 ethanol:water or 70% EtOH.

For determining percentages of components after heating GC/MS (Gas Chromatography/Mass Spectroscopy) is employed and weight percentages are determined based upon areas below curves of relevant peaks. Throughout the specification, if GC/MS was used it is so indicated.

Concentrations of sildenafil citrate are indicated as mg/ml of the relevant liquid at room temperature unless otherwise indicated.

BRIEF DESCRIPTION OF THE DRAWINGS

In order to understand the invention and to see how it may be carried out in practice, embodiments will now be described, by way of non-limiting example only, with reference to the accompanying figures. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are.

DETAILED DESCRIPTION OF EMBODIMENTS

Figure 1:
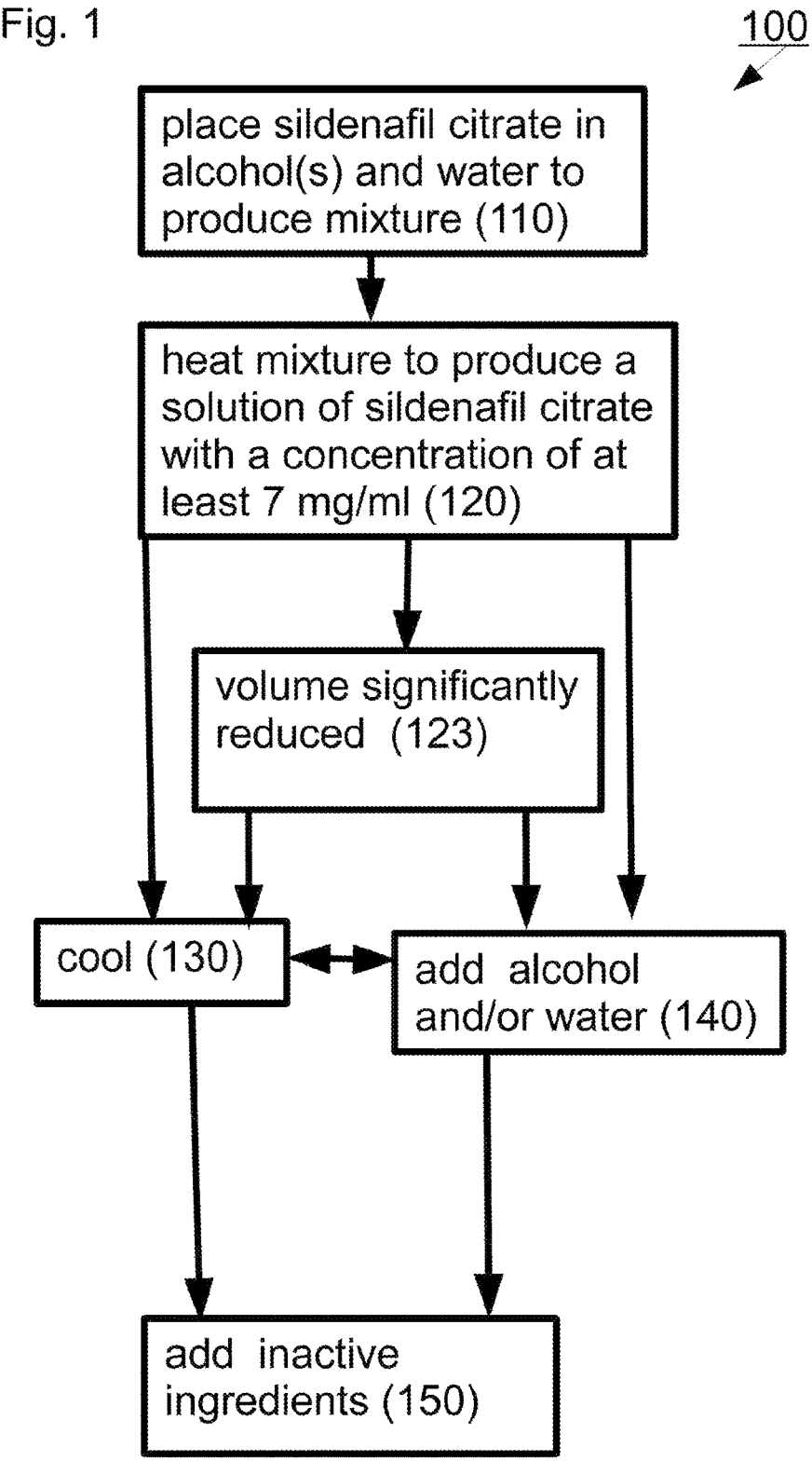
FIG. 1 is a simplified flow diagram of a preparation method according to some embodiments of the invention.

Embodiments of the invention relate to solutions of sildenafil citrate and to methods of preparing and/or using such solutions.

Specifically, some embodiments of the invention can be used to treat erectile dysfunction. In some embodiments, treatment of erectile dysfunction with a solution according to an exemplary embodiment of the invention contributes to a reduction in dosage of sildenafil citrate and/or a reduction in time between administration and onset of therapeutic effect and/or a reduction in unwanted side effects.

The principles and operation of solutions and/or methods according to exemplary embodiments of the invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Exemplary Composition

In some exemplary embodiments of the invention, there is provided a pharmaceutical composition including a liquid carrier including water and at least 20%, at least 22.5%, at least 25%, at least 25% or at least 30% of at least one alcohol with sildenafil citrate dissolved in the liquid carrier at a concentration of at least 7 mg/ml. The fact that it is possible to prepare such a composition is surprising since the solubility of sildenafil citrate in both water and alcohols which are suitable for use in pharmaceutical compositions (i.e. alcohols that are considered "safe" for human consumption) is well below 7 mg/ml. One example of an alcohol suitable for use in a pharmaceutical composition is ethanol (EtOH).

Alternatively or additionally, in some embodiments the liquid carrier includes at least 5%, at least 10%, at least 20%, at least 30%, at least 40% or at least 50% water. In some embodiments of the invention, the amount of sildenafil citrate dissolved in the liquid carrier is at least 12.5 mg/ml, at least 20 mg/ml, at least 25 mg/ml, at least 30 mg/ml, at least 40 mg/ml, at least 50 mg/ml or at least 60 mg/ml. Alternatively or additionally, in some embodiments the amount of sildenafil citrate dissolved in the liquid carrier is less than 125 mg/ml, less than 100 mg/ml, less than 70 mg/ml, less than 60 mg/ml, less than 50 mg/ml or less than 45 mg/ml.

For liquid pharmaceutical compositions in general, a small dosage volume can contribute to patient acceptance. This general preference among patients contributes to an incentive for manufacturers to produce compositions with high concentrations of sildenafil citrate (e.g. 18 mg/ml or higher).

In some exemplary embodiments of the invention, the liquid carrier includes a ketone (e.g. acetone). In some embodiments, the amount of ketone is less than the amount of water and/or ethanol in the liquid carrier. Some ketones are incompatible with glass or plastic containers during prolonged storage. For this reason, although their presence in a pharmaceutical composition is acceptable, there is no incentive to increase the amount of ketone. Among those embodiments of the invention which include a ketone (e.g. acetone), concentrations of at least 2.5%, at least 3%, at least 4%, at least 5%, at least 6%, at least 7.5%, at least 10% or at least 15% or intermediate or greater concentrations are employed. Alternatively or additionally, of those embodiments of the invention which include a ketone (e.g. acetone), concentrations of less than 50%, less than 25%, less than 15%, less than 10%, less than 7.5%, less than 5%, less than 4% or less than 3% or intermediate or lesser concentrations are employed.

Exemplary Oral Dosage Forms

Some exemplary embodiments of the invention incorporate a liquid pharmaceutical composition as described above into a non-liquid dosage form. For example, an oral dosage form according to some embodiments of the invention includes an outer coating and a liquid core including a pharmaceutical composition as described above. Oral dosage forms of this type are provided as, for example, gel caps or capsules.

Experimental data presented below in Example 5 (Table 3) demonstrate that 1 to 2 ml of liquid volume is sufficient to deliver a physiologically effective dose (20 mg to 30 mg) of sildenafil citrate in solution. However, the solutions employed in example 5 were relatively dilute. Increasing the concentration of sildenafil citrate in solution reduces the volume required for delivery of the same physiologically effective dose proportionately. For example, a 40 mg/ml solution requires only 0.5 ml to deliver a 20 mg dose. One to two gel caps can easily contain 0.5 ml of liquid volume.

Exemplary Buccal Dosage Forms

Some exemplary embodiments of the invention incorporate a liquid pharmaceutical composition as described above into buccal dosage form. It is well established that delivery of physiologically active substances through the oral mucosa can be faster and/or more effective than delivery of the same substances through the stomach and/or intestines. Some embodiments of the invention relate to a buccal dosage form including a carrier containing a pharmaceutical composition as described above provided in a wrapper adapted to prevent evaporation of the liquid carrier of the composition during storage. According to various exemplary embodiments of the invention the carrier is provided as paper, cardboard, nonwoven fabric or a wafer (e.g. starch base).

In some embodiments, the solid substrate is provided as a chewable material such as, for example, an edible wax or chewing gum. In some embodiments, the chewable material is impregnated with a liquid pharmaceutical composition as described above. Alternatively or additionally, in some embodiments the chewable material surrounds a core including a liquid pharmaceutical composition as described above.

Again experimental data presented below in Example 5 (Table 3) demonstrate that 1 to 2 ml of liquid volume is sufficient to deliver a physiologically effective dose (20 mg to 30 mg) of sildenafil citrate in solution. If a 40 mg/ml solution is employed only 0.5 ml of liquid volume provides a 20 mg dose. A 0.5 ml liquid volume can easily be provided in 1 to 2 pieces of conventional chewing gum, liquid centered chewing gum, or wax "candies".

Chewing gum containing sildenafil citrate is described at least in U.S. Pat. Nos. 6,531,114 and 6,592,850, each of which is fully incorporated by reference.

Liquid centered chewing gum is described at least in US patent application publications 20100203191 and 20100209553 and in U.S. Pat. No. 7,556,487 each of which is fully incorporated herein by reference.

Exemplary Treatment Kits

In some exemplary embodiments of the invention, a liquid pharmaceutical composition is provided in a treatment kit. In some embodiments, the treatment kit includes packaging material and/or instructions for use. In some exemplary embodiments of the invention, the instructions for use provide guidance on switching from a dose of sildenafil citrate solid to a lower dose of sildenafil in solution.

In some embodiments, the treatment kit includes a container holding a plurality of doses of a liquid pharmaceutical composition as described above and a measuring device calibrated for measurement of a single dose from the container. According to various exemplary embodiments of the invention the measuring device is configured as a cup, a spoon, or as the cap of the container. In some embodiments, calibration markings are provided (e.g. in teaspoons or ml). Optionally, the measuring device is to be totally filled (e.g. a spoon) one or more times. A measuring device which is to be filled completely during use can prevent accidentally exceeding the recommended dose. However, experimental data presented below in Example 5 (Table 3) suggests that many patients will be taking 2 to 3 times less sildenafil citrate in solution than they would consume in conventional tablet form. This means that even if they were to exceed the recommended liquid dosage by as much as 50%, the risk is expected to be low.

In some embodiments, the treatment kit includes a plurality of single doses of a liquid pharmaceutical composition as described above. According to these embodiments, each of the single doses is contained in a separate container and the kit includes packaging material adapted to hold said separate containers.

For example, in some embodiments of this type, the kit is configured as a box containing single dose ampoules (e.g. of glass or wax). A kit of this type may be configured to hold the ampoules in an ordered array (e.g. in a line). Provision of cardboard or paper dividers between ampoules may contribute to a reduction in breakage during transport and/or storage.

In some embodiments, the treatment kit is configured as a package of chewing gum with each piece of gum providing a single dose of sildenafil citrate. According to various exemplary embodiments of the invention the chewing gum is provided as sticks of conventional chewing gum, as cushions or as cubes. Cushions or cubes of gum are coated in some embodiments of the invention. Alternatively or additionally, cushions or cubes of gum are filled with a liquid center including a pharmaceutical composition according to an embodiment of the invention as described above.

In some embodiments, the treatment kit includes a nebulizer and a plurality of doses of a liquid pharmaceutical composition as described above and a measuring device calibrated for measurement of a single dose from the container to be administered via the nebulizer. According to various exemplary embodiments of the invention the measuring device is configured as described above. In certain embodiments, the nebulizer is not provided in the kit.

In some embodiments, the treatment kit includes a metered dose inhaler containing a plurality of doses of a liquid pharmaceutical composition as described above.

It is expected that delivery of a liquid pharmaceutical composition as described above via a nebulizer or metered dose inhaler will contribute to an additional reduction in the dosage which produces a therapeutic effect.

Exemplary Palatability Considerations

Sildenafil citrate is bitter. Conventional solid dosage forms, such as tablets, are typically swallowed quickly so that they are not tasted by the patient being treated. Oral administration of a liquid composition as described above and/or buccal administration of a dosage form including such a liquid composition make it more likely that the users will be sensitive to the bitter taste of sildenafil citrate.

In some exemplary embodiments of the invention, inactive ingredients are added to the composition to address this issue.

In some exemplary embodiments of the invention, a liquid pharmaceutical composition as described above includes a flavoring agent. Flavoring agents include, but are not limited to essential oils (e.g. lemon oil), sweeteners (e.g. sugars or sugar substitutes), glutamates, esters and aldehydes. Alternatively or additionally, in some embodiments a liquid pharmaceutical composition as described above includes a bitterness blocking agent. Essential oils of tarragon (e.g. *Artemesia dracunculus*) and/or basil (e.g. *Ocium basilicum*) have been found to be useful in blocking the bitterness of sildenafil citrate.

In some exemplary embodiments of the invention, 1 drop/ml of oil of tarragon, oil of basil or a combination thereof is sufficient to block the bitter taste of a liquid composition as described hereinabove and herein below (Example 5). In some embodiments, an increase in the concentration of sildenafil citrate in the composition contributes to a need to increase the amount of tarragon and/or basil oil in order to achieve the desired bitterness blocking effect.

As used in this specification and the accompanying claims the term "essential oil of tarragon" indicates CAS (Chemical Abstract Service) registry number 8016-88-4.

As used in this specification and the accompanying claims the term "essential oil of basil" indicates CAS (Chemical Abstract Service) registry number 8015-73-4.

Alternatively or additionally, in some embodiments of the invention, one or more inactive ingredients are added to provide a pleasant aroma and/or flavor (i.e. flavoring agent). For example, lemon oil, vanilla extract, oil of peppermint, oil of wintergreen, cinnamon, chocolate extract and rum extract are employed in various exemplary embodiments of the invention.

As used in this specification and the accompanying claims the term "bitterness blocking agent" indicates an ingredient which masks the bitter taste of sildenafil citrate. In some exemplary embodiments of the invention, the bitterness blocking agent serves also as a flavoring agent. In other exemplary embodiments of the invention, the bitterness blocking agent does not impart a perceptible flavor.

Exemplary liquid pharmaceutical compositions embodying the invention described hereinabove include alcohol and water. This makes them easily miscible with essential oils and/or alcohol based extracts in the relevant amounts.

First Exemplary Method of Preparation

FIG. 1 is a simplified flow diagram of an exemplary method for preparing a liquid pharmaceutical composition as described above indicated generally as 100. Depicted exemplary method 100 includes placing 110 sildenafil citrate in a combination consisting essentially of one or more alcohols and water to produce a mixture and heating 120 the mixture to produce a solution of sildenafil citrate with a concentration of at least 7 mg/ml.

As used in this specification and the accompanying claims the phrase "consisting essentially of water and one or more alcohols" indicates that other ingredients may be present but that none of these other ingredients would be expected to account for the amount of sildenafil citrate dissolved in the carrier beyond the expected solubility calculated based on the amount of water and alcohol(s). For example, "consisting essentially of water and at least one alcohol" allows for inclusion of acetone at significant concentrations because sildenafil citrate is considered to be insoluble in acetone. Conversely, "consisting essentially of water and at least one alcohol" precludes significant concentrations of dimethyl formamide or DMSO because sildenafil citrate is considered soluble in these solvents.

As used in this specification and the accompanying claims the phrase "pharmaceutical composition" precludes use of ingredients which are recognized as toxic or unsafe for human consumption in the amount needed to formulate a single dosage form of sildenafil citrate.

In some embodiments, the at least one alcohol includes ethanol. In some embodiments, alcohol is the primary alcohol. In some embodiments, ethanol is substantially the only alcohol.

Alternatively or additionally, in some embodiments the combination of alcohol(s) and water includes at least 20%, at least 30%, at least 32.5%, at least 35%, at least 37.5%, at least 40%, at least 45%, at least 50%, at least 60%, at least 70%, at least 80%, at least 90%, at least 95% alcohol(s) or intermediate or greater percentages of the one or more alcohols.

Alternatively or additionally, in some embodiments the combination of alcohol(s) and water includes at least 5%, at least 10%, at least 20%, at least 30%, at least 40%, at least 50%, at least 55%, at least 60%, at least 65%, at least 70%, at least 75%, at least 80% water or intermediate or greater percentages.

In some exemplary embodiments of the invention, heating 120 is to a temperature of at least 55° C., at least 60° C., at least 65° C., at least 70° C., at least 75° C., or intermediate or higher temperatures.

Alternatively or additionally, in some embodiments heating 120 is to a temperature not exceeding 100° C., 95° C., not exceeding 90° C., not exceeding 85° C., not exceeding 80° C., not exceeding 75° C. or intermediate or lower temperatures.

In some exemplary embodiments of the invention, heating 120 is conducted in an open container. In some embodiments, an open container permits evaporation of one or more components of the mixture. In other exemplary embodiments of the invention, heating 120 is conducted in a closed container or under a condenser. In some embodiments, the closed container/condenser contributes to a decrease in evaporation (relative to similar heating in an open container).

In some embodiments, the solution resulting from heating 120 has a sildenafil citrate concentration of at least 10.0 mg/ml, at least 12.5 mg/ml, at least 15.0 mg/ml, at least 17.5 mg/ml, at least 20.0 mg/ml, at least 22.5 mg/ml, at least 25.0 mg/ml or intermediate or higher concentrations.

In some embodiments, a volume of the solution after heating 120 is substantially the same (not depicted) as a volume of the mixture prior to heating (110). One way to achieve this is to conduct heating 120 in a closed container or under a condenser.

In other exemplary embodiments of the invention, a volume of the solution after heating 120 is significantly reduced 123 relative to the mixture prior to heating (110). One way to achieve this is to conduct heating 120 in an open container at a temperature at which one or more components of the mixture have a significant vapor pressure.

In the depicted exemplary embodiment, method 100 includes adding 140 alcohol and/or water and/or cooling the solution 130 (e.g. to room temperature). In some embodiments, cooling is performed by simply allowing the solution to cool. In some embodiments, adding 140 includes adding a mixture of alcohol and water at a desired ratio. In some embodiments, adding 140 serves to adjust the total alcohol concentration to a desired level. In some embodiments, the mixture of alcohol and water added 140 is the same ratio in which sildenafil citrate was originally placed 110. For example, in some embodiments, sildenafil citrate is placed 110 in 70% EtOH, and adding 140 also employs 70% EtOH. In other exemplary embodiments of the invention, the mixture of alcohol and water added 140 is not the same ratio in which sildenafil citrate was originally placed 110.

Alternatively or additionally, in some embodiments method 100 includes adding 150 inactive ingredients (e.g. flavoring agents and/or bitterness blockers as described above). Although adding 140 and adding 150 are depicted separately for clarity, they are conducted as a single step in many embodiments. Essential oils are easily miscible in alcohol/water combinations so that inactive ingredients can be incorporated into an alcohol/water combination employed at 140.

Second Exemplary Method of Preparation

Figure 2:
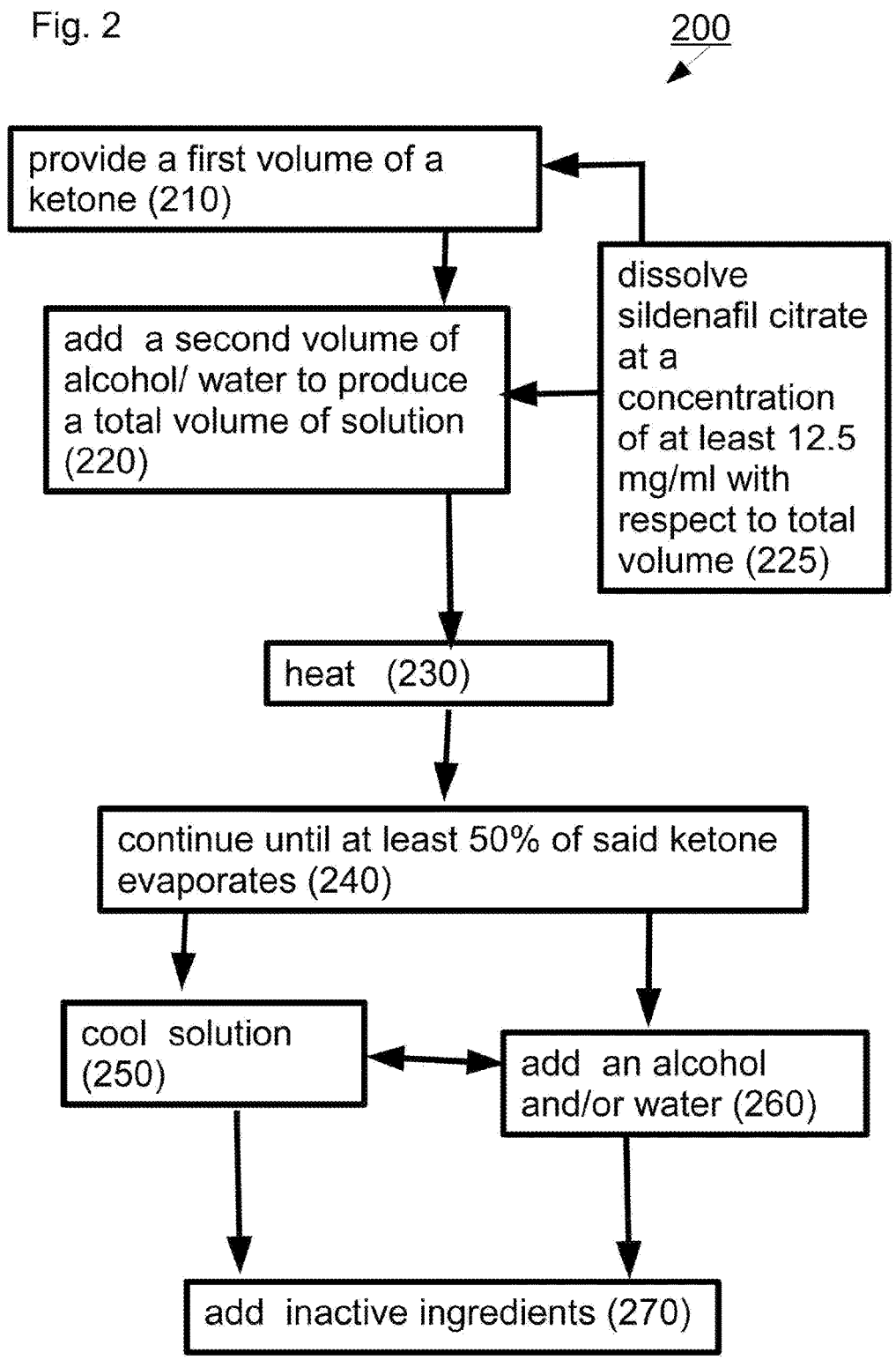
FIG. 2 is a simplified flow diagram of a preparation method according to some embodiments of the invention.

FIG. 2 is a simplified flow diagram of an exemplary method for preparing a liquid pharmaceutical composition as described above indicated generally as 200. Depicted exemplary method 200 includes providing 210 a first volume of a ketone and adding 220 a second volume consisting essentially of one or more alcohols and water (e.g. as a combination or mixture) to produce a total volume of solution and dissolving 225 sildenafil citrate at a concentration of at least 7 mg/ml, at least 10 mg/ml or at least 12.5 mg/ml with respect to the total volume. According to various exemplary embodiments of the invention dissolving 225 is in said first volume at 210 and/or in said total volume at 220. It is important to note that in many embodiments of method 200, all of the sildenafil citrate goes into solution without heating. NMR assays (see FIG. 3 and Example 4) confirmed that sildenafil citrate was unchanged by dissolution.

Some embodiments of method 200 include heating 230 the solution at a temperature not less than 10° C. below the boiling point, not less than 5° C. below the boiling point, not less than 2.5° C. below the boiling point, not less than the boiling point of the ketone or intermediate or higher temperatures. Alternatively or additionally, in some embodiments method 200 includes heating to a temperature at least 5° C. above a boiling point, at least 7.5° C. above a boiling point, at least 10° C. above a boiling point, at least 15° C. above a boiling point of said ketone or intermediate or higher temperatures.

In some embodiments, method 200 includes continuing 240 heating 230 until at least 25%, at least 50%, at least 55%, at least 60%, at least 70%, at least 80%, at least 85%, at least 90%, at least 95%, at least 97.5%, at least 99%, at least 99.5%, at least 99.75% or intermediate or greater percentages of the ketone evaporate.

In other exemplary embodiments of the invention, at least 25%, at least 50%, at least 55%, at least 60%, at least 70%, at least 80%, at least 85%, at least 90%, at least 95%, at least 97.5%, at least 99%, at least 99.5%, at least 99.75% or intermediate or greater percentages of the ketone are removed by evaporation without heating (e.g. by application of vacuum).

In other exemplary embodiments of the invention, at least 25%, at least 50%, at least 55%, at least 60%, at least 70%, at least 80%, at least 85%, at least 90%, at least 95%, at least 97.5%, at least 99%, at least 99.5%, at least 99.75% or intermediate or greater percentages of the ketone are removed by solvent extraction.

In some embodiments, the sildenafil citrate in solution at 220 has a concentration of at least 25 mg/ml, at least 30 mg/ml, at least 35 mg/ml, 40 mg/ml, at least 50 mg/ml, at least 55 mg/ml or intermediate or higher concentrations.

In some embodiments, the alcohol in the second volume (220) includes ethanol, is primarily ethanol or is substantially all ethanol.

Alternatively or additionally, in some embodiments the combination of one or more alcohols and water in the second volume (220) includes at least 20% alcohol, at least 30% alcohol, at least 32.5% alcohol, at least 35% alcohol, at least 37.5% alcohol, at least 40% alcohol or intermediate or greater percentages. Alternatively or additionally, in some embodiments the combination of an alcohol and water in the second volume (220) includes at least 60%, at least 62.5%, at least 65%, at least 67.5%, at least 70%, at least 72.5%, at least 75% water or intermediate or greater percentages.

In some embodiments, a volume of the solution after heating 230 is 50% or less of the volume of the solution prior to heating.

In the depicted exemplary embodiment, method 200 includes cooling 250 (e.g. to room temperature) the solution and/or adding 260 an alcohol and/or water to a total alcohol concentration of at least 20%, at least 300%, at least 34%, at least 40%, at least 50%, at least 60%, at least 62.5%, at least 65%, at least 67.5%, at least 70.0%, at least 72.5%, at least 75% or intermediate concentrations. Adding 260 is similar to adding 140 (FIG. 1) as described hereinabove and similar considerations apply. In some embodiments, cooling is performed by simply allowing the solution to cool.

In some embodiments, inactive ingredients are added 270. Adding 270 is similar to adding 150 (FIG. 1) as described hereinabove and similar considerations apply.

Additional Exemplary Compositions

Some embodiments of the invention relate to a pharmaceutical composition including a liquid carrier with water, ethanol, and less than 30% acetone and sildenafil citrate dissolved in the liquid carrier at a concentration of at least 10 mg/ml, at least 20 mg/ml, at least 25 mg/ml, at least 30 mg/ml, at least 35 mg/ml, at least 40 mg/ml, at least 45 mg/ml, at least 50 mg/ml, at least 55 mg/ml or intermediate or greater concentrations. In some embodiments, the concentration of acetone is less than 25% or less than 20%.

In some embodiments, the ethanol concentration is less than 90%, less than 80%, less than 70%, less than 60%, less than 50%, less than 45%, less than 40%, less than 35%, less than 30% or less than 25%. Alternatively or additionally, in some embodiments the composition contains at least 5%, at least 10%, at least 20%, at least 30%, at least 40%, at least 50%, at least 52.5%, at least 55%, at least 60%, at least 70% or intermediate or greater percentages of water.

In some embodiments, the acetone concentration is well below 20%. For example, acetone levels in the range of 5 to 7% were achieved (see Table 2 in Example 3).

Some embodiments of the invention relate to a pharmaceutical composition including a liquid carrier consisting essentially of water and at least one alcohol and sildenafil citrate dissolved in the liquid carrier at a concentration of at least 7 mg/ml. According to various exemplary embodiments of the invention the at least one alcohol includes ethanol, is primarily ethanol or is substantially only ethanol. Alternatively or additionally, in some embodiments the carrier includes residual ketone (e.g. acetone) from a preparation method which employs a ketone. An exemplary method 200 employing a ketone is described hereinabove in the context of FIG. 2.

Some embodiments of the invention relate to a pharmaceutical composition including sildenafil citrate in a liquid carrier and a bitterness blocker comprising one or more essential oils derived from a plant selected from the group consisting of tarragon and basil. In some embodiments, the sildenafil citrate is in solution. In other embodiments the sildenafil is in suspension.

These additional exemplary composition types are also provided as buccal dosage forms and/or treatment kits as described above in additional exemplary embodiments of the invention.

Exemplary Treatment Method

Figure 4:
FIG. 4 is a simplified flow diagram of a method according to some exemplary embodiments of the invention.

FIG. 4 is a simplified flow diagram of an exemplary treatment method for erectile dysfunction indicated generally as 400.

Depicted exemplary method 400 includes identifying 410 a patient taking a customary dose of sildenafil citrate in solid form for erectile dysfunction and Treating 420 said patient for erectile dysfunction with sildenafil citrate in solution using a reduced dose which is less than 50% of the customary dose.

In some exemplary embodiments of the invention, the sildenafil citrate is in solution in a liquid carrier including one or more alcohols and water. According to various exemplary embodiments of the invention the one or more alcohols include ethanol, include primarily ethanol or is substantially all ethanol.

Alternatively or additionally, in some embodiments the liquid carrier includes a ketone (e.g. acetone).

According to various exemplary embodiments of the invention the reduced dose is delivered in a volume of less than 15 ml, less than 10 ml, less than 5 ml, less than 3 ml, less than 2 ml or intermediate or smaller volumes. According to various exemplary embodiments of the invention administration of the reduced dose is via an oral or a buccal route. Buccal dosage forms and/or treatment kits as described hereinabove are a convenient way to provide the reduced dose.

It is expected that during the life of this patent many dosage forms for pharmaceutically active ingredients in liquid form will be developed and the scope of the invention is intended to include all such new dosage forms a priori.

Alternatively or additionally, it is expected that during the life of this patent many carriers for buccal administration of pharmaceutically active ingredients will be developed and the scope of the invention is intended to include all such carriers a priori.

As used herein the term "about" refers to ±10%.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Specifically, a variety of numerical indicators have been utilized. It should be understood that these numerical indicators could vary even further based upon a variety of engineering principles, materials, intended use and designs incorporated into the various embodiments of the invention. Additionally, components and/or actions ascribed to exemplary embodiments of the invention and depicted as a single unit may be divided into subunits. Conversely, components and/or actions ascribed to exemplary embodiments of the invention and depicted as sub-units/individual actions may be combined into a single unit/action with the described/depicted function.

Alternatively, or additionally, features used to describe a method can be used to characterize an apparatus and features used to describe an apparatus can be used to characterize a method.

It should be further understood that the individual features described hereinabove can be combined in all possible combinations and sub-combinations to produce additional embodiments of the invention. The examples given above are exemplary in nature and are not intended to limit the scope of the invention.

Each recitation of an embodiment of the invention that includes a specific feature, part, component, module or process is an explicit statement that additional embodiments not including the recited feature, part, component, module or process exist. Specifically, the invention has been described in the context of ethanol and water, or ethanol, water and acetone but might also be used with other alcohols and/or other ketones.

All publications, references, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The terms "include", and "have" and their conjugates as used herein mean "including but not necessarily limited to".

Additional objects, advantages, and novel features of various embodiments of the invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions; illustrate the invention in a non limiting fashion.

Example 1

Preparation of Sidenafil Citrate Solutions at High Concentration

In order to demonstrate the feasibility of dissolving sildenafil citrate at high concentrations in a combination of solvents that are considered separately as poor solvents for the compound, a series of ten experiments using ethanol (EtOH), water and acetone in various proportions was conducted.

In each of experiments 1 to 6, 250 mg of sildenafil citrate (Teva Pharmaceuticals; Israel) was dissolved in a mixture of acetone and EtOH/water as indicated in Table 1 and heated at 70 to 77° C. for 10 minutes in an open container.

In experiments 7-10, 150-250 mg of sildenafil citrate (Teva Pharmaceuticals; Israel) was dissolved in 70% EtOH/water and heated at 70 to 77° C. for 10 minutes in a closed container.

Results presented in Table 1 indicate that it is possible to achieve initial concentrations of 12.5 mg/ml of Sildenafil citrate in solution without heating (Experiments 1, 2 and 6) and up to 25 mg/ml with heating (Experiment 7).

In experiment 11, 900 mg of sildenafil citrate (Teva Pharmaceuticals; Israel) was dissolved in 50 ml of 70% EtOH/water for 15 minutes at room temperature using an Ultrasonic bath (Elma Elmasonic S 30 H).

In experiment 12, 900 mg of sildenafil citrate (Teva Pharmaceuticals; Israel) was dissolved in 50 ml of 70% EtOH/water at 40° C. for 2 minutes in an open container.

In experiment 13, 900 mg of sildenafil citrate (Teva Pharmaceuticals; Israel) was dissolved in 50 ml of 70% EtOH/water for 15 minutes up to 35° C. using an Ultrasonic bath (Elma Elmasonic S 30 H).

In addition, as heating continued and the volume of solvent mixture decreased, the sildenafil citrate remained in solution at concentrations as high as 35.7 mg/ml. Due to the relative vapor pressures of the components of the liquid mixture, the relative proportion of water in the mixture increased as the volume decreased.

Some solutions were filtered using filter paper and/or 0.22 microns membrane filters with no visible residue.

This example illustrates that the solubility of Sildenafil citrate in EtOH/water, or EtOH/water with small amounts of residual acetone, is far greater than its solubility in water or EtOH or acetone alone.

TABLE 1 solubility of sildenafil citrate in EtOH/water mixtures with and without acetone

| | Initial composition | | | | | | After heating | |
|---|---|---|---|---|---|---|---|---|
| Exp. | sildenafil citrate (mg) | Acetone (ml) | 60% EtOH (ml) | 70% EtOH (ml) | Total vol. (ml) | Initial conc. (mg/ml) | Need Heat to dissolve? | Vol. post heating (ml) | Final conc. (mg/ml) |
| 1 | 250 | 10 | 10 | — | 20 | 12.5 | NO | 7 | 35.7 |
| 2 | 250 | 10 | — | 10 | 20 | 12.5 | NO | 9 | 27.8 |
| 3 | 250 | 3 | — | 10 | 13 | 19.2 | YES | 7 | 35.7 |
| 4 | 250 | 4 | — | 10 | 14 | 17.9 | YES | 7 | 35.7 |
| 5 | 250 | 5 | — | 10 | 15 | 16.7 | YES | 7 | 35.7 |
| 6 | 250 | 10 | — | 10 | 20 | 12.5 | NO | 7 | 35.7 |
| 7 | 250* | — | — | 10 | 10 | 25.0 | YES | 10* | 25.0 |
| 8 | 200* | — | — | 10 | 10 | 20.0 | YES | 10* | 20.0 |
| 9 | 180* | — | — | 10 | 10 | 18.0 | YES | 10* | 18.0 |
| 10 | 150* | — | — | 10 | 10 | 15.0 | YES | 10* | 15.0 |
| 11 | 900 | — | — | 50 | 50 | 18.0 | NO | 50 | 18.0 |

TABLE 1-continued solubility of sildenafil citrate in EtOH/water mixtures with and without acetone

| | Initial composition | | | | | | After heating | |
|---|---|---|---|---|---|---|---|---|
| Exp. | sildenafil citrate (mg) | Acetone (ml) | 60% EtOH (ml) | 70% EtOH (ml) | Total vol. (ml) | Initial conc. (mg/ml) | Need Heat to dissolve? | Vol. post heating (ml) | Final conc. (mg/ml) |
| 12 | 900 | — | — | 50 | 50 | 18.0 | YES | 50 | 18.0 |
| 13 | 900 | — | — | 50 | 50 | 18.0 | NO | 47 | 18.0 |

*dissolution and heating in closed container to prevent evaporation

Example 2

Stability of Sildenafil Citrate Solutions

The volume of each solution from experiments 1 to 7 in Example 1 was adjusted to 10 ml with 60% EtOH (Experiment 1) or 70% EtOH (Experiments 2-7) to produce a clear solution with a concentration of 25 mg/ml. After 24 hours all solutions remained clear. Some of these solutions have remained clear for two years. Some solutions were filtered using filter paper and/or 0.22 microns membrane filters with no visible residue.

In order to assess the stability of these further they were subjected to freezing at minus 18° C. and thawing. The solution from experiment 7 exhibited a slight degree of sedimentation after thawing. The solutions from experiment 1 to 6 remained clear after thawing. The solutions from experiments 3, 6, and 9 & 10 remained clear after 3 cycles of freezing and thawing. Solutions 9 and 10 remained clear after 6 months.

This example illustrates that the solubility of sildenafil citrate is not diminished by freezing and thawing and suggests that the solutions will have a significant shelf life (e.g. 2 years or more).

Example 3

Solvent Concentrations after Heating

In order to assess the solvent concentrations in the sildenafil citrate solutions after heating, samples were sent to an independent laboratory for GC/MS (Gas Chromatography/Mass Spectroscopy) analysis.

Three samples were prepared as follows:

Sample A: 250 mg sildenafil citrate+10 ml acetone+10 ml 70% EtOH in water was heated to 77° C. for 7 min., till volume reduced to 5 ml (50 mg/ml). 70% EtOH in water was added to bring the volume to 10 ml (25 mg/ml).

Sample B: 500 mg sildenafil citrate+10 ml acetone+10 ml 70% EtOH in water was heated to 77° C. for 7 min., till volume reduced to 5.1 ml (98 mg/ml). 70% EtOH in water was added to bring the volume to 10 ml (50 mg/ml).

Sample C: 10 ml acetone+10 ml 70% EtOH in water was heated to 77° C. for 7 min., till volume reduced to 5.3 ml. 70% EtOH in water was added to bring the volume to 10 ml.

Sample C served as a control to see if the sildenafil citrate influenced relative evaporation rates of the different solvents.

Results presented in Table 2 indicate that small but measurable amounts of acetone remained after heating until volume had been reduced by 75% at a temperature well above the boiling point of acetone.

The actual acetone concentration remaining in the samples was approximately double the percentage in table 2, since the samples were diluted after heating with an acetone free solution.

Similarly, results presented in Table 2 indicate that measurable amounts of EtOH remained after heating until volume had been reduced by 75% at a temperature well above the boiling point of EtOH.

The actual EtOH concentration remaining in the samples was actually much less than the percentage indicated by GC/MS, since the samples were diluted after heating with 70% EtOH. The number in parentheses indicates the EtOH % resulting from this dilution.

TABLE 2 solvent percentages after heating as analyzed by GC/MS

| Sample | EtOH (from dilution) | Acetone | Water (by difference) | pH |
|---|---|---|---|---|
| A | 36.6% (35.0%) | 6.31% | 57.09% | 4.51 |
| B | 36.0% (34.3%) | 6.17% | 57.83% | 4.55 |
| C | 38.5% (32.9%) | 5.73% | 55.77% | 4.47 |

Preparation of samples A and B indicates that it is possible to achieve concentration of 50 to 100 mg/ml of sildenafil citrate in solution. The pH of solutions A, B and C was in the range of 4.4 to 4.55.

This example illustrates that the achieved solution concentrations of sildenafil citrate cannot be accounted for by the nominal solubility of that compound in any of the three components of the solvent mixture.

Sample B was not stable long term. During shipping to the outside laboratory that performed the GC/MS some sedimentation had occurred (apparently due to freezing (at up to −55 degrees Celsius) in transit). Warming prior to testing re-dissolved the sediment.

Example 4

Stability of Sildenafil Citrate During Heating

In order to confirm that sildenafil remained unchanged by heating in solvent mixtures as described in Examples 1 and 3, samples that were solubilized as described above were subject to NMR analysis using commercially available sildenafil citrate (Teva Pharmaceuticals; Israel) dissolved in DMSO as a control.

Figure 3:
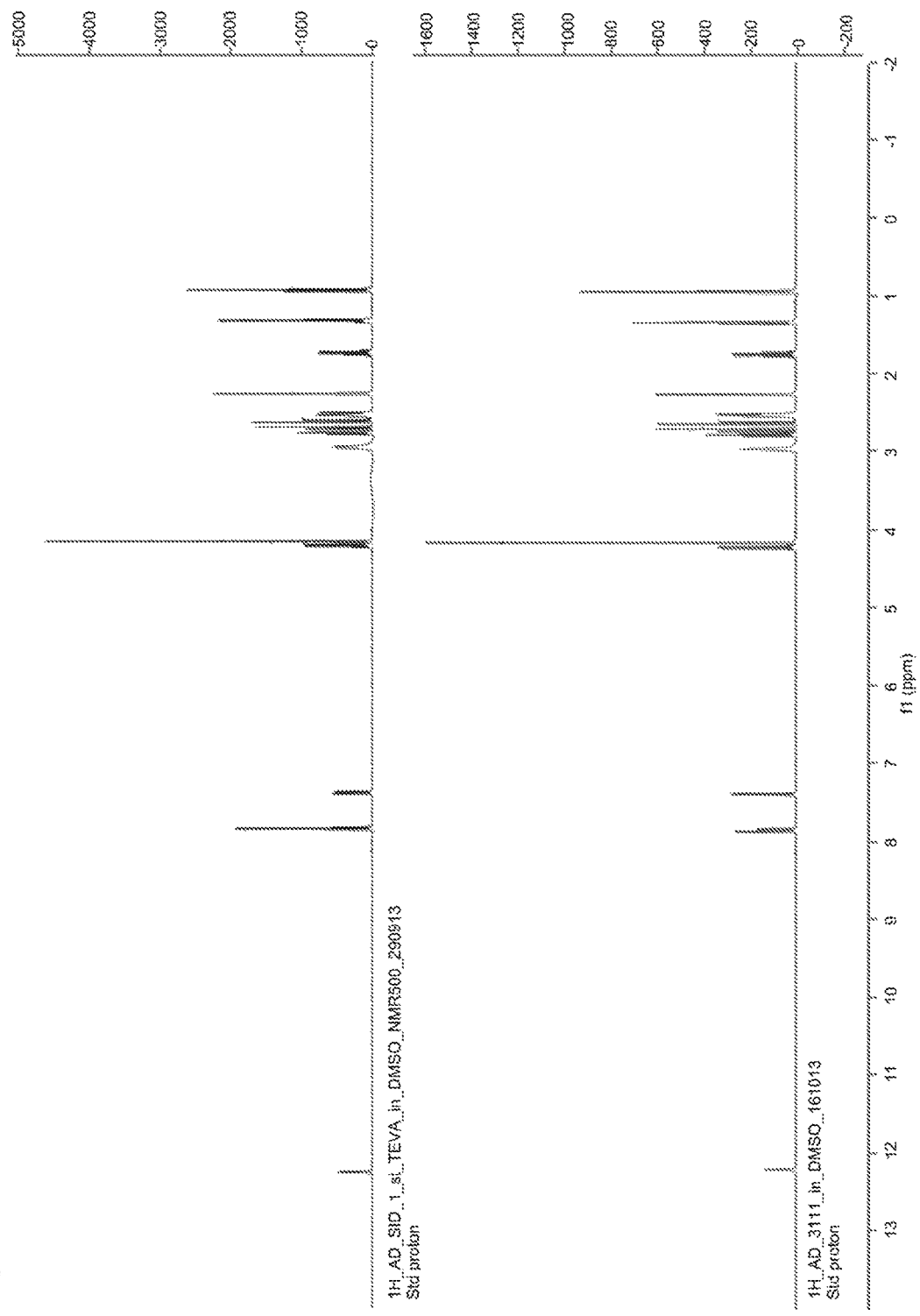
FIG. 3 is an NMR (Nuclear Magnetic Resonance) plot of a liquid pharmaceutical composition of sildenafil citrate according to an exemplary embodiment of the invention aligned with a plot of sildenafil citrate powder.

Representative NMR results are shown in FIG. 3. In the figure, one trace is sildenafil citrate in solution according to an exemplary embodiment of the invention and the other trace is the control material. The two traces are substantially identical.

This example illustrates that the protocols described above cause no chemical change in sildenafil citrate.

Example 5

Exemplary Case Studies

In order to evaluate the efficacy of sildenafil citrate solutions according to exemplary embodiments of the invention in human subjects the following solutions were prepared:

Solution 1—sildenafil citrate was dissolved in equal volumes of 70% EtOH and acetone and heated in an open container to allow evaporation of about 65% of the initial volume. The resultant concentrated solution was diluted with 70% EtOH to produce a final concentration of 20 mg/ml of sildenafil citrate.

Solution 2—sildenafil citrate was heated in 70% EtOH in a closed container resulting in a final concentration of 15 mg/ml of sildenafil citrate.

TABLE 3

Human subjects

| Subject | Age | diagnosis | Previous treatment | Experimental treatment | Efficacy maintained? |
|---|---|---|---|---|---|
| A | 52 | erectile dysfunction | 50 mg pill | 1 ml sol. 1 (20 mg) | YES |
| B | 57 | type II diabetes, erectile dysfunction | 100 mg pill | 1.5 ml sol. 1 (30 mg) | YES |
| C | 64 | erectile dysfunction | 100 mg pill | 2 ml sol. 2 (30 mg) | YES |

Subject A was a regular user of VIAGRA® 50 mg pills for approximately one year. A 1 ml dose of solution 1 according to an exemplary embodiment of the invention produced the same therapeutic effect with a dosage reduction of 2.5×. Furthermore, solution 1 according to an exemplary embodiment reportedly produced onset of action in 10 minutes, as opposed to approximately 30 to 40 minutes using VIAGRA® 50 mg pills.

Subject B was a regular user of VIAGRA® 100 mg pills for erectile dysfunction. A 1.5 ml dose of solution 1 according to an exemplary embodiment of the invention produced the same therapeutic effect with a dosage reduction of more than 3.0×. Subject B also reported no headaches using solution 1 according to an exemplary embodiment of the invention although VIAGRA® pills caused headaches. Subject B also reported onset of action in 10-15 minutes, about half the time it took for onset of action using pills.

Subject C had regularly used VIAGRA® 100 mg pills over a period of 5 years. He achieved equivalent therapeutic effect using 2 ml (30 mg active ingredient) of Solution 2 according to an exemplary embodiment of the invention. Like subject B, he reported no headaches whereas VIAGRA® pills caused headaches. Like the other two subjects, he reported onset of action in 10 to 15 minutes, about half to a third of the time it took for onset of action using VIAGRA® pills.

These results suggest increased efficacy/unit of sildenafil citrate in solution administered orally according to exemplary embodiments of the invention relative to conventional tablet dosage forms. This suggests increased bioavailability. In addition, sildenafil citrate in solution administered orally appears to produce less side effects. It is not clear if this is due to the lower dosages or other factors. Alternatively or additionally, onset of action using sildenafil citrate in solution administered orally produced a more rapid onset of therapeutic effect than conventional solid dosage forms, despite the lower dose.

Solutions 1 and 2 contained essential oils as described above to block bitterness. Subjects A, B and C found the taste of the solutions acceptable.

Example 6

Preparation of Additional Sildenafil Citrate Solutions at High Concentration

In order to investigate the contribution of alcohol and water for dissolving sildenafil citrate at high concentrations an additional series of ten experiments using ethanol (EtOH) and water in various proportions was conducted with 50% acetone in the initial composition.

In this series of experiments, sildenafil citrate was dissolved in an initial volume of a liquid carrier and heated at 70 to 77° C. to reduce the volume. As in Example 1, as the volume decreased, the relative proportion of water in the mixture increased.

Results presented in table 4 indicate that it is possible to achieve a concentration of 12.5 mg/ml to 37.5 mg/ml by adding sildenafil citrate to a mixture that is half acetone and half 30% to 60% EtOH. No heat was required to produce solutions with these initial concentrations in any of the experiments. Heating these mixtures until the volume was reduced to 7 ml produced solutions with concentrations of 35 mg/ml to 107 mg/ml.

TABLE 4 solubility of sildenafil citrate in EtOH/ water mixtures at various ratios with acetone

| | Initial composition | | | | | | After heating | |
|---|---|---|---|---|---|---|---|---|
| Exp. | sildenafil citrate (mg) | Acetone (ml) | EtOH/ water mixture (ml) | % EtOH in mixture | Total vol. (ml) | Initial conc. (mg/ml) | Vol. post heating (ml) | Conc. (mg/ml) |
| 1 | 250 | 10 | 10 | 60 | 20 | 12.5 | 7 | 35.7 |
| 2 | 400 | 10 | 10 | 60 | 20 | 20.0 | 7 | 57.1 |
| 3 | 500 | 10 | 10 | 60 | 20 | 25.0 | 7 | 71.4 |
| 4 | 250 | 10 | 10 | 50 | 20 | 12.5 | 7 | 35.7 |
| 5 | 500 | 10 | 10 | 50 | 20 | 25.0 | 7 | 71.4 |
| 6 | 750 | 10 | 10 | 50 | 20 | 37.5 | 7 | 107.1 |
| 7 | 500 | 10 | 10 | 40 | 20 | 25.0 | 7 | 71.4 |
| 8 | 750 | 10 | 10 | 40 | 20 | 37.5 | 7 | 107.1 |
| 9 | 500 | 10 | 10 | 30 | 20 | 25.0 | 7 | 71.4 |
| 10 | 750 | 10 | 10 | 30 | 20 | 37.5 | 7 | 107.1 |

This example illustrates that it is possible to decrease the amount of alcohol used relative to Example 1.

Example 7

Stability of Additional Sildenafil Citrate Solutions

The volume of each solution from experiments 1 to 10 in Example 6 was adjusted to 10 ml with the same EtOH/water mixture used to prepare the initial composition. In all ten experiments the resultant solution was clear. Adjusted concentrations were 25 mg/ml to 75 mg/ml.

After 24 hours at room temperature, these solutions exhibited varying degrees of cloudiness and/or sedimentation.

This example illustrates that development of commercially relevant exemplary embodiments based on experiments 1 to 10 in the previous example may employ stabilizing agents to keep the sildenafil citrate in solution.

Known stabilizing agents include, but are not limited to: Diacetylated monoglycerides, diethyl glycol monopalmitostearate, glyceryl behenate, glyceryl distearate, glyceryl monolinoleate, glyceryl mono-oleate, glyceryl monostearate, self emulsifying glyceryl monostearate. macrogol cetostearyl ethers, cetomacrogol 1000, 9 polyoxyl 20 cetostearyl ether, macrogol 15 hydroxystearate, macrogol lauril ethers, laureth 4, lauromacrogol 400, macrogol monomethyl ethers, macrogol oleyl ethers, polyoxyl 10 oleyl ether, macrogol stearates, polyoxyl 40 stearates, menfegol, mono & di glycerides, nonoxinols, octoxinols, poloxamers, polyoxyl castor oil, polyoxyl hydrogenated castor oils, polysorbates, propylen glycol diacetate, propylen glycol laureates, propylen glycol dilaurate, propylen glycol mono laureate, propylen glycol monopalmitostearate, quillaia, sorbitan esters, sucrose esters, tyloxapol, carrageenan, cellulose, ceratonia, dextrates, ethylcellulose, gastric mucin, hyprolose, hypromellose, hypermellose phthalate, methylcellulose, polyethylene oxide, polyvinyl acetate, polyvinyl alcohol, silicas, sodium starch glycolate, tragacanth, xanthan gum.

Example 8

Sildenafil Citrate Solutions with Varying Amounts of Acetone

In order to investigate the contribution of acetone for dissolving sildenafil citrate at high concentrations an additional series of thirteen experiments using ethanol (EtOH) and water in various proportions with relatively small amounts of acetone was conducted.

In this series of experiments, sildenafil citrate was dissolved in an initial volume of a liquid carrier and heated at 70 to 77° C. either to dissolve the sildenafil citrate (experiments 6 and 13) or to reduce the volume (experiment 1-5 and 7-12). In this series of experiments, the initial volume was 10 ml and heating was continued until the volume was reduced to 9 ml (experiments 1-5) or 7 ml (experiments 7-12). As in Example 1, as the volume decreased, the relative proportion of water in the mixture increased.

In this series of experiments, heating was required for initial dissolution of the sildenafil citrate at initial concentrations of 16.7 mg/ml to 50 mg/ml.

Results summarized in table 5 indicate that it was possible to achieve an initial concentration of 40 mg/ml using 10% acetone (experiment 6); 50 mg/ml using 2% to 8% acetone in 50% to 70% EtOH (experiments 3 to 5) and 25 mg/ml using 6.3% acetone in 35% EtOH (experiment 13).

In each of the thirteen experiments in this example the sildenafil citrate was in solution at the end of the heating.

TABLE 5 solubility of sildenafil citrate in EtOH/water mixtures at various ratios with acetone

| | Initial composition | | | | | After heating | |
| --- | --- | --- | --- | --- | --- | --- | --- |
| Exp. | sildenafil citrate (mg) | Acetone (ml) | % EtOH/ H₂0 added | Total vol. (ml) | Initial conc. (mg/ml) | Vol. post heating (ml) | Conc. (mg/ml) |
| 1 | 250 | 0.2 | 50 | 10 | 25 | 9 | 27.8 |
| 2 | 250 | 0.6 | 50 | 10 | 25 | 9 | 27.8 |
| 3 | 500 | 0.2 | 50 | 10 | 50 | 9 | 55.6 |
| 4 | 500 | 0.6 | 50 | 10 | 50 | 9 | 55.6 |
| 5 | 500 | 0.8 | 70 | 10 | 50 | 9 | 55.6 |
| 6* | 400 | 1.0 | 95 | 10 | 40 | 10 | 40.0 |
| 7 | 500 | 4.0 | 70 | 14 | 35.7 | 7 | 71.4 |
| 8 | 500 | 5.0 | 70 | 15 | 33.3 | 7 | 71.4 |
| 9 | 250 | 2.0 | 70 | 12 | 20.8 | 7 | 71.4 |
| 10 | 250 | 3.0 | 70 | 13 | 19.2 | 7 | 35.7 |
| 11 | 250 | 4.0 | 70 | 14 | 17.9 | 7 | 35.7 |
| 12 | 250 | 5.0 | 70 | 15 | 16.7 | 7 | 35.7 |
| 13* | 250 | 0.63 | 35 | 10 | 25.0 | 10 | 25.0 |

*Heated a 70-77° C. only to point of dissolution

Example 9

Stability of Low Acetone Sildenafil Citrate Solutions

The volume of each solution from experiments 1 to 13 in Example 8 was adjusted to 10 ml with 50% EtOH/water (experiments 1 to 4); 70% EtOH/water (experiments 5, 7, 8 and 9 to 13) and 95% EtOH/water (experiment 6). In all thirteen experiments the resultant solution was clear. Concentrations were 25 mg/ml to 50 mg/ml.

After 24 hours at room temperature, some solutions exhibited sedimentation but the diluted solutions from experiments 10 to 13 remained clear.

This example illustrates that it is possible to decrease the amount of acetone used relative to Example 1.

Example 10

Sildenafil Citrate Solutions without Ketone

In order to investigate the possibility of dissolving sildenafil citrate at high concentrations in alcohol/water mixtures without a ketone, an additional series of eight experiments using ethanol (EtOH) and water in various proportions with no acetone was conducted.

In this series of experiments, sildenafil citrate was placed in 10 ml of EtOH/water and heated at 70 to 77° C. to dissolve the sildenafil citrate (experiments 1 to 8) and/or to reduce the volume (experiments 1 to 5) or heated at 70 to 77° C. in a closed container to dissolve the sildenafil citrate while preventing evaporation (experiments 6 to 8). As in Example 1, if heating was conducted in an open container, as the volume decreased, the relative proportion of water in the mixture increased.

In this series of experiments, heating was required for initial dissolution of the sildenafil citrate at initial concentrations of 25 mg/ml to 50 mg/ml.

Results summarized in table 6 indicate that it was possible to achieve a final concentration of 55.6 mg/ml without acetone by performing the initial dissolution in 50% to 70% EtOH (experiments 2 and 3) and 50 mg/ml without acetone by performing the initial dissolution 35% EtOH (experiment 7). In each of the eight experiments in this example the sildenafil citrate was in solution at the end of the heating.

TABLE 6 solubility of sildenafil citrate in EtOH/water mixtures at various ratios without acetone

| | Initial composition | | | After heating | |
|---|---|---|---|---|---|
| Exp. | sildenafil citrate (mg) | % EtOH | Initial conc. (mg/ml) | Vol. (ml) | Conc. (mg/ml) |
| 1 | 250 | 50 | 25 | 9 | 27.8 |
| 2 | 500 | 50 | 50 | 9 | 55.6 |
| 3 | 500 | 70 | 50 | 9 | 55.6 |
| 4 | 250 | 70 | 25 | 7 | 35.7 |
| 5 | 300 | 70 | 30 | 7 | 42.9 |
| 6 | 250 | 70 | 25 | 10 | 25 |
| 7 | 500 | 35 | 50 | 10 | 50 |
| 8 | 250 | 35 | 25 | 10 | 25 |

Example 11

Stability of Acetone Free Sildenafil Citrate Solutions

The volume of each solution from experiments 1 to 8 in Example 10 was adjusted to 10 ml with 50% EtOH/water (experiments 1 and 2) and 70% EtOH/water (experiments 3 to 5). No adjustment of volume was needed in experiments 6 to 8. In all 8 experiments the resultant solution was clear. Concentrations were 25 mg/ml to 50 mg/ml.

After 24 to 48 hours at room temperature, some solutions exhibited sedimentation and/or cloudiness but the diluted solution from experiment 4 remained clear.

This example illustrates that solutions of sildenafil citrate at concentrations well above those reported in the literature for water or ethanol can be achieved using a mixture of water and ethanol and heating.

Experiments with similar compounds such as TADALAFIL or VARDENAFIL using the same methodology described above were not successful in yielding stable solutions.

Example 12

Sildenafil Citrate Solutions Contain No Undissolved Sildenafil Citrate

In order to confirm that sildenafil citrate was actually in solution, as opposed to in suspension, an 18 mg/ml sildenafil citrate solution (In 70% ethanol; solution 9; Table 1) was subjected to spectrophotometric analysis at 228 nm before and after filtration via a 0.22 micron filter (Membrane solutions MSPES syringe filter). Results are summarized in Table 7. A UV-VIS Genesys 10S Thermo Scientific spectrophotometer was used for the assay. Samples were placed in a UV Kurette Halbmicro/UV Cuvette semi micro [Cat no: 759150] for reading.

The 228 nm wavelength is recognized as being the absorbance maxima for sildenafil citrate (see Baokar, Shrikrishna et al. (Research J. Pharm and Tech (2012) 5.2). 70% ethanol was used as a calibration blank.

Because the reference describes measurements at μg/ml concentrations, both the filtered and unfiltered 18 mg/ml solutions were diluted to 9 μg/ml and 12.5 μg/ml and measured again.

TABLE 7

Absorbance of sildenafil citrate solutions with and without microfiltration

| # of samples | Concentration of sildenafil citrate solution | Absorbance units (A) 228 n Mean ± σ | |
|---|---|---|---|
| | | unfiltered | filtered |
| 3 | 18 mg/ml | 3.807 ± 0.005 | 3.813 ± 0.005 |
| 3 | 9 μg/ml | 0.201 ± 0.005 | 0.197 ± 0.005 |
| 6 | 12.5 μg/ml | 0.202 ± 0.005 | 0.206 ± 0.005 |

Results presented in Table 7 indicate that filtration did not remove insoluble sildenafil citrate. This example establishes that sildenafil citrate as prepared in Example 1 is fully soluble at 18 mg/ml.

The invention claimed is:

1. A pharmaceutical composition comprising: (a) a liquid carrier comprising water and at least 35% of ethanol; and (b) sildenafil citrate dissolved in said liquid carrier at a concentration of at least 7 mg/ml.

2. A pharmaceutical composition according to claim 1, wherein said concentration of sildenafil citrate dissolved in said liquid carrier is at least 12.5 mg/ml.

3. A pharmaceutical composition according to claim 2, wherein said concentration of sildenafil citrate dissolved in said liquid is at least 20 mg/ml.

4. An oral dosage form comprising: an outer coating; and a liquid core comprising a pharmaceutical composition according to claim 1.

5. A buccal dosage form comprising: a carrier containing a pharmaceutical composition according to claim 1; and a wrapper adapted to prevent evaporation of said liquid carrier during storage.

6. A treatment kit comprising: a plurality of single doses of a pharmaceutical composition according to claim 1, each of said single doses contained in a separate container; and packaging material adapted to hold said separate containers.

7. A pharmaceutical composition according to claim 1, comprising at least 50% ethanol.

8. A pharmaceutical composition according to claim 7, wherein said concentration of sildenafil citrate dissolved in said liquid carrier is at least 12.5 mg/ml.

9. A pharmaceutical composition according to claim 8, wherein said concentration of sildenafil citrate dissolved in said liquid is at least 20 mg/ml.

10. A pharmaceutical composition according to claim 1, stable for at least 24 hours.

11. A pharmaceutical composition according to claim 1, wherein said liquid carrier has a pH of ≥4.4.

12. A pharmaceutical composition according to claim 8, stable for at least 24 hours.

13. A pharmaceutical composition according to claim 8, wherein said liquid carrier has a pH of ≥4.4.

14. A pharmaceutical composition comprising: (a) a liquid carrier comprising water, at least 35% ethanol, and 0.0075% to 20% acetone; and (b) sildenafil citrate dissolved in said liquid carrier at a concentration of at least 10 mg/ml.

15. A pharmaceutical composition according to claim 14, wherein said liquid carrier comprises at least 2.5% acetone.

16. A pharmaceutical composition according to claim 14, comprising at least 60% ethanol.

17. A pharmaceutical composition according to claim 14, stable for at least 24 hours.

18. A pharmaceutical composition according to claim 14, wherein said liquid carrier has a pH of ≥4.4.

19. A pharmaceutical composition according to claim 14, further comprising a stabilizing agent.

20. A pharmaceutical composition according to claim 14, wherein said stabilizing agent is selected from the group consisting of: diacetylated monoglycerides, diethyl glycol monopalmitostearate, glyceryl behenate, glyceryl distearate, glyceryl monolinoleate, glyceryl mono-oleate, glyceryl monostearate, self emulsifying glyceryl monostearate. macrogol cetostearyl ethers, cetomacrogol 1000, 9 polyoxyl 20 cetostearyl ether, macrogol 15 hydroxystearate, macrogol lauril ethers, laureth 4, lauromacrogol 400, macrogol monomethyl ethers, macrogol oleyl ethers, polyoxyl 10 oleyl ether, macrogol stearates, polyoxyl 40 stearates, menfegol, mono & di glycerides, nonoxinols, octoxinols, poloxamers, polyoxyl castor oil, polyoxyl hydrogenated castor oils, polysorbates, propylen glycol diacetate, propylen glycol laureates, propylen glycol dilaurate, propylen glycol mono laureate, propylen glycol monopalmitostearate, quillaia, sorbitan esters, sucrose esters, tyloxapol, carrageenan, cellulose, ceratonia, dextrates, ethylcellulose, gastric mucin, hyprolose, hypromellose, hypermellose phthalate, methylcellulose, polyethylene oxide, polyvinyl acetate, polyvinyl alcohol, silicas, sodium starch glycolate, tragacanth, xanthan gum.

\* \* \* \* \*